United States Patent [19]

Kay

[11] 3,931,164
[45] Jan. 6, 1976

[54] HETEROCYCLIC COMPOUNDS
[75] Inventor: Ian Trevor Kay, Wokingham, England
[73] Assignee: Imperial Chemical Industries Limited, London, England
[22] Filed: Oct. 25, 1974
[21] Appl. No.: 518,216

[30] Foreign Application Priority Data
Nov. 7, 1973 United Kingdom............... 51595/73
Jan. 24, 1974 United Kingdom................. 3267/74

[52] U.S. Cl............................. 260/249.5; 424/249
[51] Int. Cl.² ...................................... C07D 251/42
[58] Field of Search ................................ 260/249.5

[56] References Cited
UNITED STATES PATENTS
3,887,552  6/1975  Stahle et al. .................... 260/249.5

Primary Examiner—John M. Ford
Attorney, Agent, or Firm—Cushman, Darby & Cushman

[57] ABSTRACT

Heterocyclic compounds of formula:

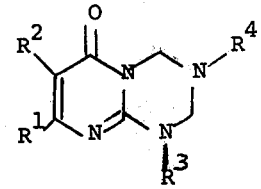

wherein $R^1$, $R^2$ and $R^3$ are alkyl, and $R^4$ is selected from alkyl, alkenyl, aralkyl, cycloalkyl, aryl and carboxyalkyl. The compounds and compositions comprising them have pesticidal, particularly fungicidal, utility.

3 Claims, No Drawings

HETEROCYCLIC COMPOUNDS

This invention relates to novel heterocyclic compounds, their preparation, compositions comprising them and their use as pesticides.

Accordingly the present invention provides heterocyclic compounds of formula:

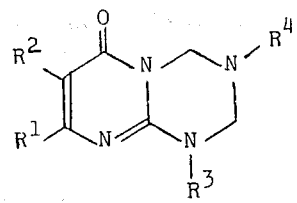

wherein $R^1$ and $R^2$ which may be the same or different, are hydrogen, halogen or alkyl, or together represent an alkylene group of from 3 to 6 carbon atoms; $R^3$ is hydrogen or alkyl; and $R^4$ is alkyl, alkenyl, aralkyl, cycloalkyl, aryl or carboxyalkyl.

Preferably $R^1$, $R^2$ and $R^3$ represent alkyl groups containing from 1 to 6 carbon atoms. Examples of such groups are methyl, ethyl, propyl, butyl and amyl groups.

Preferably $R^4$ represents an alkyl group containing from 1 to 20 carbon atoms, such as the methyl, ethyl, propyl, butyl, octyl or octadecyl groups; it may also represent the benzyl, allyl, cyclohexyl, phenyl or carboxymethyl group.

An especially preferred group of compounds are those wherein $R^1$ is methyl, $R^2$ is n-butyl and $R^3$ is ethyl.

Specific compounds which are embraced by the present invention include those listed in Table 1 below, where the meanings of $R^1$, $R^2$, $R^3$ and $R^4$ are given together with the melting point for each compound.

TABLE I

| Compound No. | $R^1$ | $R^2$ | $R^3$ | $R^4$ | Melting Point °C |
|---|---|---|---|---|---|
| 1 | $CH_3$ | $C_4H_9(n)$ | $C_2H_5$ | $CH_3$ | 89 |
| 2 | $CH_3$ | $C_4H_9(n)$ | $C_2H_5$ | $C_4H_9(i)$ | 75 |
| 3 | $CH_3$ | $C_4H_9(n)$ | $C_2H_5$ | $C_8H_{17}(n)$ | 40 |
| 4 | $CH_3$ | $C_4H_9(n)$ | $C_2H_5$ | $CH_2CH=CH_2$ | 98 |
| 5 | $CH_3$ | $C_4H_9(n)$ | $C_2H_5$ | cyclohexyl | 93 |
| 6 | $CH_3$ | $C_4H_9(n)$ | $C_2H_5$ | $C_{18}H_{37}(n)$ | 74 |
| 7 | $CH_3$ | $C_4H_9(n)$ | $C_2H_5$ | $CH_2C_6H_5$ | 106 |
| 8 | $CH_3$ | $C_4H_9(n)$ | $C_2H_5$ | $C_6H_5$ | 104 |
| 9 | $CH_3$ | $C_4H_9(n)$ | $C_2H_5$ | $C_2H_5$ | 81 |
| 10 | $CH_3$ | $C_4H_9(n)$ | $C_2H_5$ | $C_3H_7(i)$ | 66 |
| 11 | $CH_3$ | $C_4H_9(n)$ | $C_2H_5$ | $C_3H_7(n)$ | 96 |
| 12 | $CH_3$ | $C_4H_9(n)$ | $C_2H_5$ | $CH_2COOH$ | 128 |

The novel heterocyclic compounds of the invention are useful as pesticides, and are particularly useful as fungicides for the control of fungal pathogens of plants, for example, for combating the mildew diseases of cereals such as *Erysiphe graminis*.

The present invention also provides a process for the preparation of the novel heterocyclic compounds which comprises treating a compound of formula:

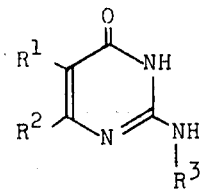

wherein $R^1$ and $R^2$, which may be the same or different, are hydrogen, halogen, or alkyl or together represent an alkylene group of from 3 to 6 carbon atoms and $R^3$ is hydrogen or alkyl, with formaldehyde and a primary amine of formula $R^4NH_2$, wherein $R^4$ is alkyl, alkenyl, aralkyl, cycloalkyl, aryl or carboxyalkyl.

Preferably $R^1$, $R^2$ and $R^3$ represent lower alkyl containing from 1 to 6 carbon atoms, such as for example, methyl, ethyl, propyl, butyl and amyl groups.

The above process may involve dissolving or suspending the compound of formula:

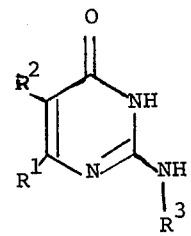

in a suitable solvent or diluent and thereafter treating it with formaldehyde, preferably in the form of an aqueous solution, and with a primary amine. The formaldehyde and the primary amine may be added to the dissolved or suspended compound either together or, preferably, sequentially, allowing a period of time to elapse after addition of the formaldehyde before adding the primary amine. The reaction by which the novel heterocyclic compounds may be prepared may be performed at temperatures within the range 0° to 150°C. Preferably the reaction mixture is heated to, say, the reflux temperature of the solvent or diluent used, for at least part of the time to facilitate acceleration of the reaction. A suitable solvent for use in the process is a lower alcohol, for example, methanol.

Examples of primary amines useful in the performance of the process of the invention include primary alkylamines such as methylamine, propylamine, isopropylamine, ethylamine, isobutylamine, octylamine, and octadecylamine; primary aralkylamines such as benzylamine; primary alkenylamines such as allylamine; primary cycloalkylamines such as cyclohexylamine; arylamines, such as aniline; and amino acid derivatives such as glycine.

This invention also relates to pesticidal compositions and to methods of combating fungal pests of plants.

According to the present invention, pesticidal compositions comprise as an active ingredient a compound of the formula:

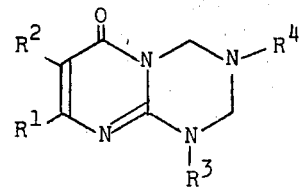

wherein $R^1$, $R^2$, $R^3$ and $R^4$ have any of the meanings set out hereinbefore, in association with an agriculturally and horticulturally acceptable diluent or carrier.

Of particular interest are compositions comprising compounds in which $R^1$ is methyl, $R^2$ is n-butyl and $R^3$ is ethyl. Particular compounds which may be used in the compositions of the present invention are those set out in Table 1 above.

The compositions may be in the form of dusting powders wherein the active ingredient is mixed with a solid diluent or carrier, for example, kaolin, bentonite, kieselguhr, or talc, or they may be in the form of granules, wherein the active ingredient is absorbed on a porous granular material, for example, pumice.

Alternatively, the compositions may be in the form of liquid preparations to be used as dips or sprays, which are generally aqueous dispersions or emulsions of the active ingredient in the presence of one or more known wetting agents, dispersing agents or emulsifying agents. These compositions are prepared by dissolving the active ingredient in a suitable solvent, for example, a ketonic solvent such as diacetone alcohol, and adding the mixture so obtained to water which may contain one or more wetting, dispersing or emulsifying agents.

The compositions which are to be used in the form of aqueous dispersions or emulsions are generally supplied in the form of a concentrate containing a high proportion of the active ingredient, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment. The concentrates may contain 10–85% by weight of the active ingredient. When diluted to form aqueous preparations, such preparations may contain varying amounts of the active ingredient depending upon the purpose for which they are to be used.

For agricultural or horticultural purposes, aqueous preparations containing between 0.001% and 1.0% by weight of the active ingredient may be used.

The compositions of the present invention may, if desired, also comprise in addition to a compound of the present invention, at least one other biologically-active ingredient, for example, an insecticide or a fungicide.

In use the compositions are applied to the pests, to the locus of the pests, to the habitat of the pests or to growing plants liable to infestation by the pests, by any of the known means of applying pesticidal compositions, for example, by dusting or spraying.

The compositions of the invention are useful in the control of fungal diseases of plants, including, for example, the following:

Botrytis cinerea (gray mould of tomato)
Phytophthora infestans (blight of tomato)
Puccinia recondita (rust of wheat)
Plasmopara viticola (powdery mildew of vines)
Uncinula necator (downy mildew of vines)
Podosphaera leucotricha (powdery mildew of apples)
Sphaerotheca fuliginea (powdery mildew of cucumbers)
Erysiphe graminis (powdery mildew of wheat/barley)

The invention is illustration by the following examples.

EXAMPLE 1

This Example illustrates the preparation of Compound no. 1 of Table 1 from 5-n-butyl-2-ethylamino-6-methyl-3,4-dihydropyrimidin-4-one.

5-n-butyl-2-ethylamino-6-methyl-3,4-dihydropyrimidine-4-one (4.30 g.) was dissolved in methanol (50 ml.) and formaldehyde (40% w/v solution in water, 3.0 ml.) added at the ambient temperature (ca. 22°C). The mixture was stirred for 30 minutes and then methylamine (25% w/v solution in water, 2.48 ml.) was added, after which the mixture was heated at the reflux temperature for a further 30 minutes. The solvent was removed from the mixture by evaporation under reduced pressure and the residual solid dissolved in dichloromethane (50 ml.), the dichloromethane solution washed twice with sodium hydroxide solution (5% w/v solution in water, 2 × 50 ml.) and with water (50 ml.) and finally dried over anhydrous sodium sulphate. Removal of the dichloromethane by evaporation under reduced pressure, yielded an oil which rapidly crystallised, and which was recrystallised from petroleum ether (boiling range 60°–80°C) to yield Compound No. 1 of Table 1, melting point 89°C.

EXAMPLE 2

The procedure of Example 1 was used to obtain Compound nos. 2 to 7 of Table 1, as follows:

Compound no. 2 of Table 1 was obtained from 5-n-butyl-2-ethylamino-6-methyl-3,4-dihydropyrimidin-4-one and isobutylamine. The product melted at 75°C.

Compound no. 3 of Table 1 was obtained from 5-n-butyl-2-ethylamino-6-methyl-3,4-dihydropyrimidin-4-one and n-octylamine. The product melted at 40°C.

Compound no. 4 of Table 1 was obtained from 5-n-butyl-2-ethylamino-6-methyl-3,4-dihydropyrimidin-4-one and allylamine. The product melted at 98°C.

Compound no. 5 of Table 1 was obtained from 5-n-butyl-2-ethylamino-6-methyl-3,4-dihydropyrimidin-4-one and cyclohexylamine. The product melted at 93°C.

Compound no. 6 of Table 1 was obtained from 5-n-butyl-2-ethylamino-6-methyl-3,4-dihydropyrimidin-4-one and n-octadecylamine. The product melted at 74°C.

Compound no. 7 of Table 1 was obtained from 5-n-butyl-2-ethylamino-6-methyl-3,4-dihydropyrimidin-4-one and benzylamine. The product melted at 106°C.

Compound no. 8 of Table 1 was obtained from 5-n-butyl-2-ethylamino-6-methyl-3,4-dihydropyrimidin-4-one and aniline. The product melted at 104°C.

Compound no. 9 of Table 1 was obtained from 5-n-butyl-2-ethylamino-6-methyl-3,4-dihydropyrimidin-4-one and ethylamine. The product melted at 81°C.

Compound no. 10 of Table 1 was obtained from 5-n-butyl-2-ethylamino-6-methyl-3,4-dihydropyrimidin-4-one and isopropylamine. The product melted at 66°C.

Compound no. 11 of Table 1 was obtained from 5-n-butyl-2-ethylamino-6-methyl-3,4-dihydropyrimidin-4-one and n-propylamine. The product melted at 96°C.

Compound no. 12 of Table 1 was obtained from 5-n-butyl-2-ethylamino-6-methyl-3,4-dihydropyrimidin-4-one and glycine. The product melted at 128°C.

EXAMPLE 3

5 parts by weight of Compound no. 1 of Table 1 were thoroughly mixed in a suitable mixer with 95 parts by weight of talc. There was thus obtained a dusting powder.

EXAMPLE 4

10 parts by weight of Compound no. 5 of Table 1, 10 parts of an ethylene oxide-octylphenol condensate ("Lissapol" NX; "Lissapol" is a Trade Mark) and 80 parts by weight of diacetone alcohol were thoroughly mixed. There was thus obtained a concentrate which, on mixing with water, gave an aqueous dispersion suitable for application as a spray in the control of fungal pests of plants.

EXAMPLE 5

A granular composition was prepared by dissolving the active ingredient in a solvent, spraying the solution obtained on to the granules of pumice and allowing the solvent to evaporate.

|  | % wt. |
|---|---|
| Compound No. 3 of Table 1 | 5 |
| Pumice Granules | 95 |
|  | 100 |

EXAMPLE 6

An aqueous dispersion formulation was prepared by mixing and grinding the ingredients recited below in the proportions stated.

|  | % wt. |
|---|---|
| Compound No. 5 of Table 1 | 40 |
| Calcium lignosulphonate | 10 |
| Water | 50 |
|  | 100 |

EXAMPLE 7

The compounds of this invention were tested against a variety of foliar fungal diseases of plants. The technique employed is to spray the foliage of the undiseased plants with a solution of the test compound and also to drench the soil in which the plants are growing with another solution of the same test compound. All solutions for spraying and drenching contained 0.01% of the test compound. The plants were then infected with the disease it was desired to control and after a period of days, depending upon the particular disease, the extent of the disease was visually assessed. The results are given in Table 3 below, wherein the extent of the disease is given in the form of a grading as follows:

| Grading | Percentage Amount of Disease |
|---|---|
| 0 | 61 to 100 |
| 1 | 26 to 60 |
| 2 | 6 to 5 |
| 3 | 0 to 5 |

In Table 2 the disease is given in the first column, and in the second column is given the time which elapsed between infecting the plants and assessing the amount of disease.

TABLE 2

| Disease and Plant | Time Interval (days) | Disease Code Letter (Table 3) |
|---|---|---|
| Phytophthora infestans (tomato) | 3 | B |
| Plasmopara viticola (vine) | 7 | C |
| Podosphaera leucotricha (apple) | 10 | D |
| Uncinula necator (vine) | 10 | E |
| Botrytis cinerea (bean) | 3 | F |

TABLE 3

| Compound No. Table 1 | Disease Code letter Table 2 | | | | |
|---|---|---|---|---|---|
|  | B | C | D | E | F |
| 1 | 2 | 0 | 3 | 1 | 0 |
| 2 | 0 | 0 | 1 | 3 | 3 |
| 4 | 0 | 2 | 3 | 1 | 1 |
| 5 | 0 | 1 | 3 | 0 | 1 |
| 8 | 0 | 3 | 0 | 0 | 0 |
| 9 | 1 | 3 | 3 | 0 | — |
| 10 | — | 3 | 3 | 0 | — |
| 11 | 3 | 3 | 3 | 3 | — |
| 12 | 3 | 3 | 3 | 0 | 0 |

All the compounds were found to be active against *Sphaerotheca fuliginea* (powdery mildew of cucumber) and *Erysiphe graminis* (powdery mildew of barley) in tests to determine the protectant activity of the compounds at a rate of 50 ppm.

I claim:
1. A compound of formula:

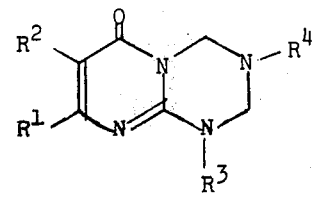

wherein $R^1$, $R^2$ and $R^3$ are alkyl groups of from one to six carbon atoms and $R^4$ is an alkyl group of from one to 20 carbon atoms or benzyl, allyl, cyclohexyl, phenyl or carboxymethyl.

2. A compound according to claim 1 wherein $R^1$ is methyl, $R^2$ is n-butyl and $R^3$ is ethyl.

3. A process for the preparation of a compound as defined in claim 1 which comprises the steps of
   a. suspending or dissolving a compound of formula

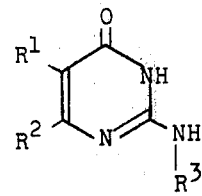

in a diluent or solvent selected from the group consisting of lower alcohols and water,
   b. treating said suspended or dissolved compound with at least a stoichiometric amount of formaldehyde in the form of an aqueous solution thereof, and with at least a stoichiometric amount of a primary amine of formula R⁴NH₂;
c. heating the reaction mixture thus produced to the reflux temperature of the diluent or solvent for a period to accelerate the reaction, and
d. recovering from the mixture the compound of formula:
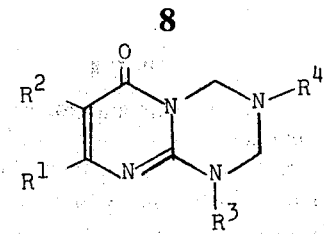
thus produced; wherein $R^1$, $R^2$, $R^3$ and $R^4$ have any of the meanings given in claim 1.
* * * * *